United States Patent [19]
Brors

[11] Patent Number: 5,291,030
[45] Date of Patent: Mar. 1, 1994

[54] OPTOELECTRONIC DETECTOR FOR CHEMICAL REACTIONS

[75] Inventor: Daniel L. Brors, Byron, Calif.

[73] Assignee: Torrex Equipment Corporation, Livermore, Calif.

[21] Appl. No.: 894,315

[22] Filed: Jun. 4, 1992

[51] Int. Cl.[5] ............................................. G01N 15/06
[52] U.S. Cl. .................................... 250/573; 356/436
[58] Field of Search ............... 250/564, 565, 573, 575; 356/436, 437

[56] References Cited

U.S. PATENT DOCUMENTS

| | | | |
|---|---|---|---|
| 3,592,607 | 7/1971 | Bruce | 250/573 |
| 3,992,109 | 11/1976 | Bock | 250/573 |
| 4,224,405 | 9/1980 | Hijikata | 356/436 |
| 4,629,903 | 12/1986 | Giacobbe et al. | 250/573 |
| 4,782,226 | 11/1988 | Jeffries, Jr. et al. | 250/227 |
| 4,908,676 | 3/1990 | Bedell et al. | 250/573 |

Primary Examiner—David C. Nelms
Attorney, Agent, or Firm—Skjerven, Morrill, MacPherson, Franklin & Friel

[57] ABSTRACT

Changes in the state of a chemical reactant, particularly a resin used for purifying gases, are measured by directing a beam of light through the reactant and detecting changes in the light transmissivity of the reactant as the reactant goes from a first state to a second state.

10 Claims, 6 Drawing Sheets

OPTOELECTRONIC DETECTOR FOR CHEMICAL REACTIONS

FIELD OF THE INVENTION

This invention relates to the optoelectronic detection of chemical reactions within a sealed container and particularly to reactions relating to gas purification.

BACKGROUND OF THE INVENTION

Pure gases are a critical component in many industrial processes today. Gas purity is typically measured as the quantity of all contaminants as a percentage of the total, e.g., 99.9999% (referred to as "6 nines pure"), or the quantity of individual impurities in ppm (parts per million) or ppb (parts per billion).

Industry requirements for the purity of gases are continually increasing. Many gases are now required to be "8 or 9 nines" pure. Such purity requirements are very difficult to achieve in the initial purification process, and they are almost impossible to maintain to the point of use after the gas has been put into a gas cylinder, and the cylinder has been shipped to the customer and attached to an appropriate gas regulator and gas piping. The gas cylinder, regulator and piping are all sources of contamination.

One way to provide gases of required purity at the point of use is to perform a final purification process immediately before use. An efficient and cost-effective purification process at the point of use involves passing the gas through a chemically reactive resin bed that chemically absorbs certain impurities, such as oxygen, water vapor or hydrocarbons. The resins are typically placed in a stainless steel cylinder which has appropriate pipe fittings such that the cylinder containing the resin can be placed in the gas line for a final purification.

One problem associated with the use of a resin is determining when the resin has become chemically depleted and no longer able to purify the gas. A solution is to install equipment such as residual gas analyzers, spectrometers or other electronic instruments to measure gas purity at the point of use. In most cases, however, such a solution is prohibitively expensive.

Another solution involves observing some physical change that occurs in certain resins when they become chemically depleted. For example, Saes Corporation manufactures a resin whose electrical conductivity changes as the resin becomes chemically depleted. A purification module includes the resin in a stainless steel container, with appropriate pipe fittings and a resistance gauge to determine when the resin is depleted. U.S. Pat. No. 4,782,226 describes a gas purification module containing a resin whose reflectivity changes as the resin is depleted. The reflectivity is monitored and the purification module is replaced when the reflectivity measurements indicate that the resin has become depleted.

There are several weaknesses with both of these methods. Most resins which are used for gas purification purposes are not electrically conductive. Furthermore, using electrical conductivity to measure resin depletion requires an electrical connection to the resin. Many gases requiring purification are extremely corrosive and it is therefore very difficult to maintain a good electrical connection in such an environment. Also, many resins do not exhibit a change in reflectivity with resin depletion or exhibit such a small change in reflectivity that detecting the change requires very sensitive instruments.

Accordingly, it is an object of the present invention to provide a means of determining resin depletion that does not rely on the conductivity or reflectivity of the resin.

SUMMARY OF THE PRESENT INVENTION

The present invention is based on the phenomenon that many resins and other chemicals exhibit a change in light transmissivity as they become depleted or as their state otherwise changes. For example, a resin supplied by Millipore Corporation of Bedford, Mass. is opaque when it is reactive and translucent when it is chemically depleted. Starting with a fresh reactive resin, the intensity of transmitted light changes by several orders of magnitude as the resin becomes depleted.

In a preferred embodiment according to this invention, a container for a resin includes a means for transmitting a beam of light and a means for receiving the transmitted light after it has passed through the resin. The light is transmitted into the resin through a transparent window which is attached to a tube extending through a wall of the container. The light is received through a second transparent window which is attached to a second tube that also extends through the container wall. The windows are placed an optimal distance apart so as to maximize the difference between the amount of light transmitted through the resin when it is in its reactive (opaque) state and the amount of light that is transmitted through the resin when it is in its depleted (translucent) state.

An optical fiber provides a convenient means for transmitting the light to the first window and for receiving the light from the second window. A first optical fiber is used to transmit the light from a light source to the first window. A second optical fiber is used to transmit the light from the second window to an electronic receiver where the intensity of the light is compared to known values that correspond to the reactive and depleted states of the resin.

An advantage of this invention is that the use of light transmitted through the resin provides for excellent electronic signal descrimination between the chemically reactive resin and the depleted resin.

DESCRIPTION OF THE INVENTION

Figure 1:
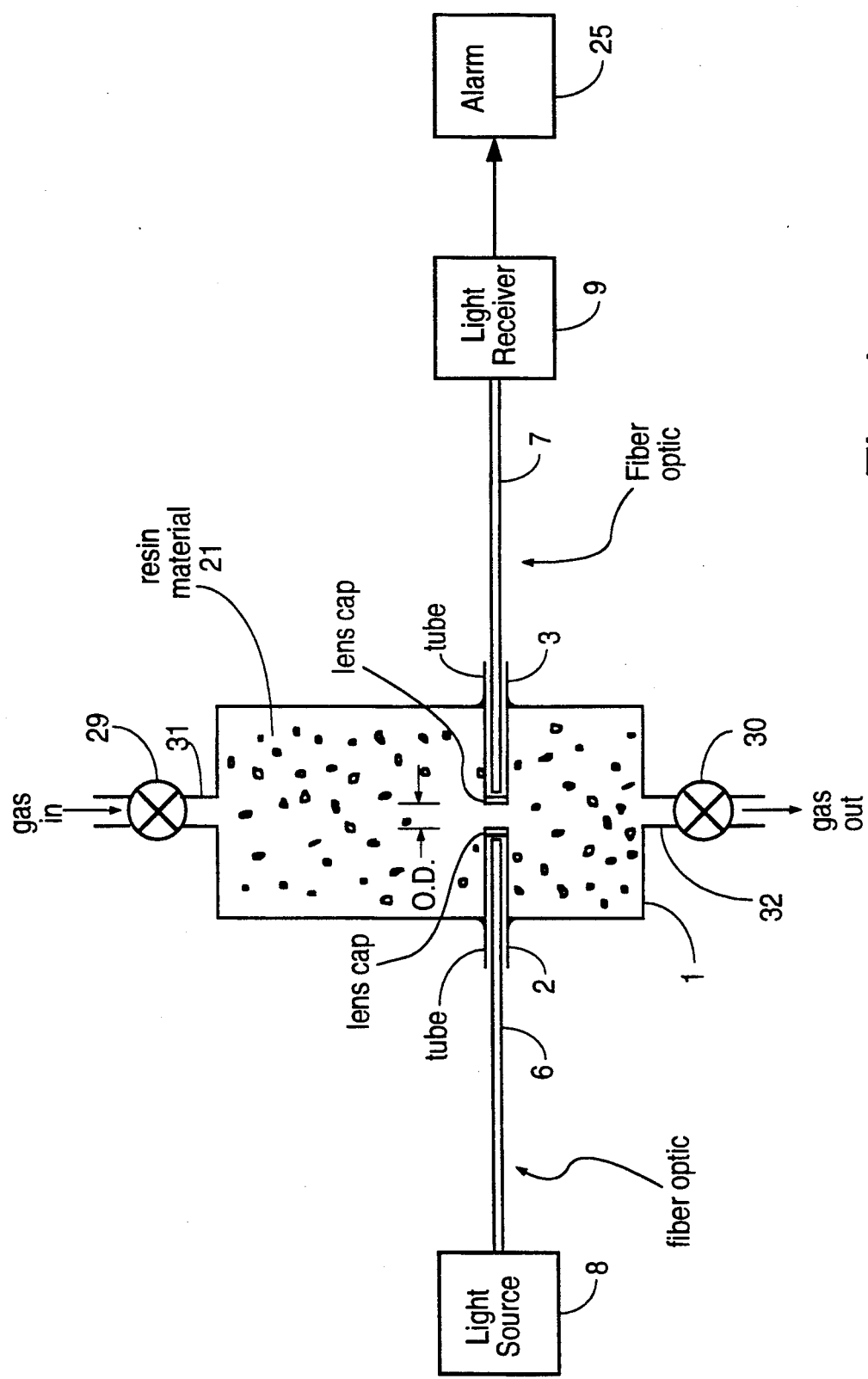
FIG. 1 illustrates a block drawing of a purification module in accordance with the invention, including the appropriate electronics.

FIG. 1 shows a purification module, which includes a metal resin container 1 through which a gas to be purified is passed. Metal tubes 2 and 3 are inserted into holes in the wall of the container and welded in place to form a gas tight seal between tubes 2 and 3 and container 1.

Lens caps 4 and 5 are welded to the ends of tubes 2 and 3 to form a gas tight seal. This is advantageously done before tubes 2 and 3 are inserted into container 1. A light source 8 is attached to an optical fiber 6 which runs through tube 2 and transmits light to lens cap 4. An optical fiber 7 runs through tube 3 from a light receiver 9 to lens cap 5. Lens cap 4 and lens cap 5 are separated by a predetermined distance D such that light leaving lens cap 4 passes through a resin 21 inside container 1 and is received at lens cap 5. The spacing D of lens cap 4 and lens cap 5 is discussed below. An output of light receiver 9 (a photosensor with electronic amplification) is directed to an alarm 25. Light receiver 9 electronically compares the light received at lens cap 5 to preset levels representing the known amount of light absorbed by resin 21 when it is in its reactive (opaque) state or its depleted (translucent) state. Light receiver 9 transmits a signal to alarm 25 when the amount of light received indicates that resin 21 has been depleted and requires changing.

Figure 2:
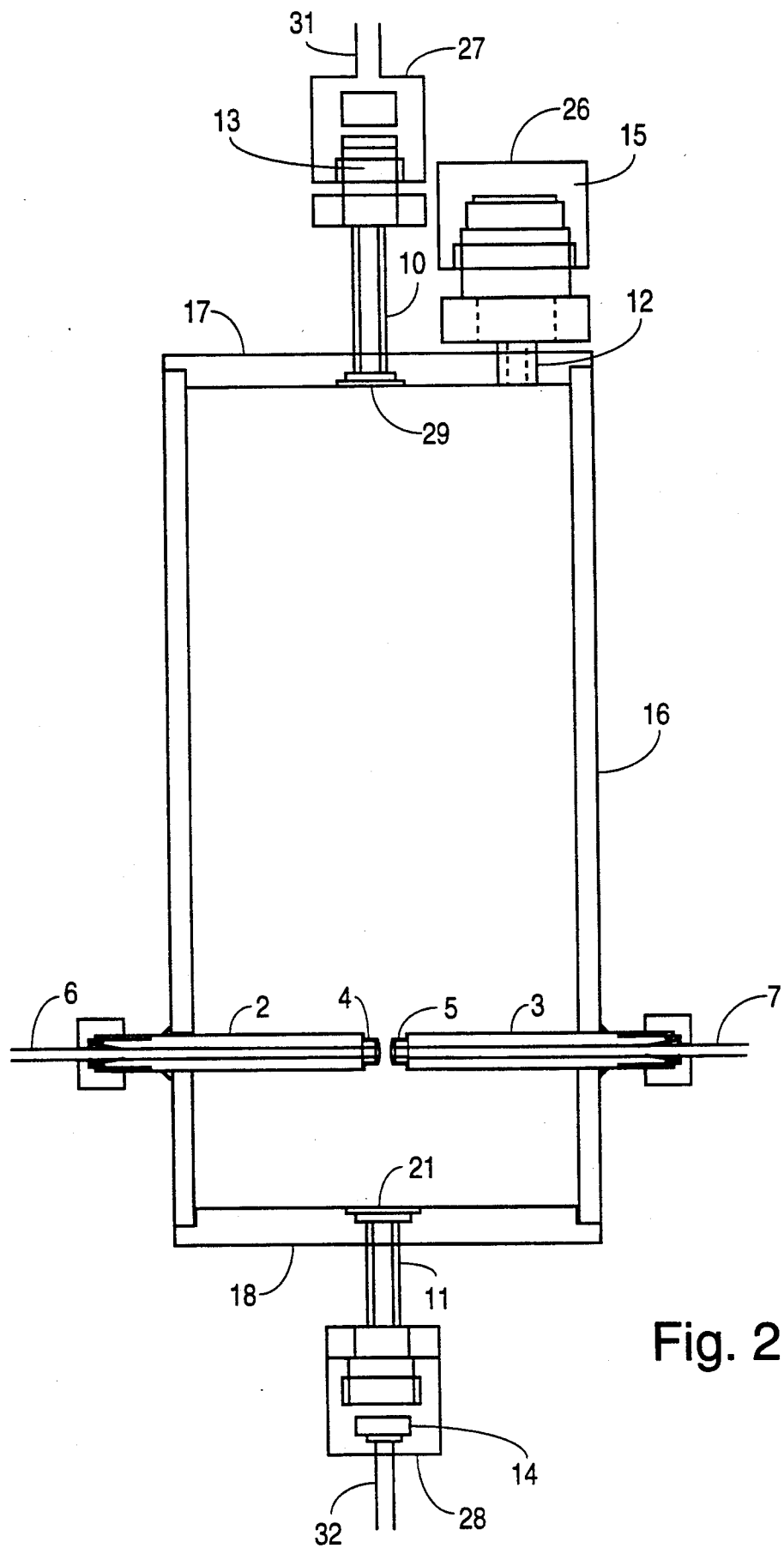
FIG. 2 illustrates a cross-sectional view of the purification container.

FIG. 2 illustrates a cross-sectional view showing the construction of container 1. Container 1 includes a metal cylinder 16 to which a metal top 17 and a metal bottom 18 have been welded to form a gas tight vessel. A metal inlet gas tube 10 with a gas line fitting 13 (typically a VCR fitting) is welded to top 17 to form a gas tight seal. An outlet gas tube 11 with a gas line fitting 14 is welded to bottom 18 to form a gas tight seal. A tube 12 is also welded to top 17. Tube 12 has a fitting 15 and a removable cap 26 and is used to fill container 1 with resin 21 and is sealed with cap 26 to form a gas tight seal. Cap 26 is a screw cap. A nut 27 screws onto fitting 13 to form a gas tight seal; nut 27 is attached to a tube 31 and tube 31 is attached to a valve 29. Similarly, a nut 28 is screwed onto fitting 14, and nut 28 is attached to a tube 32 which is attached to a valve 30.

Figure 3:
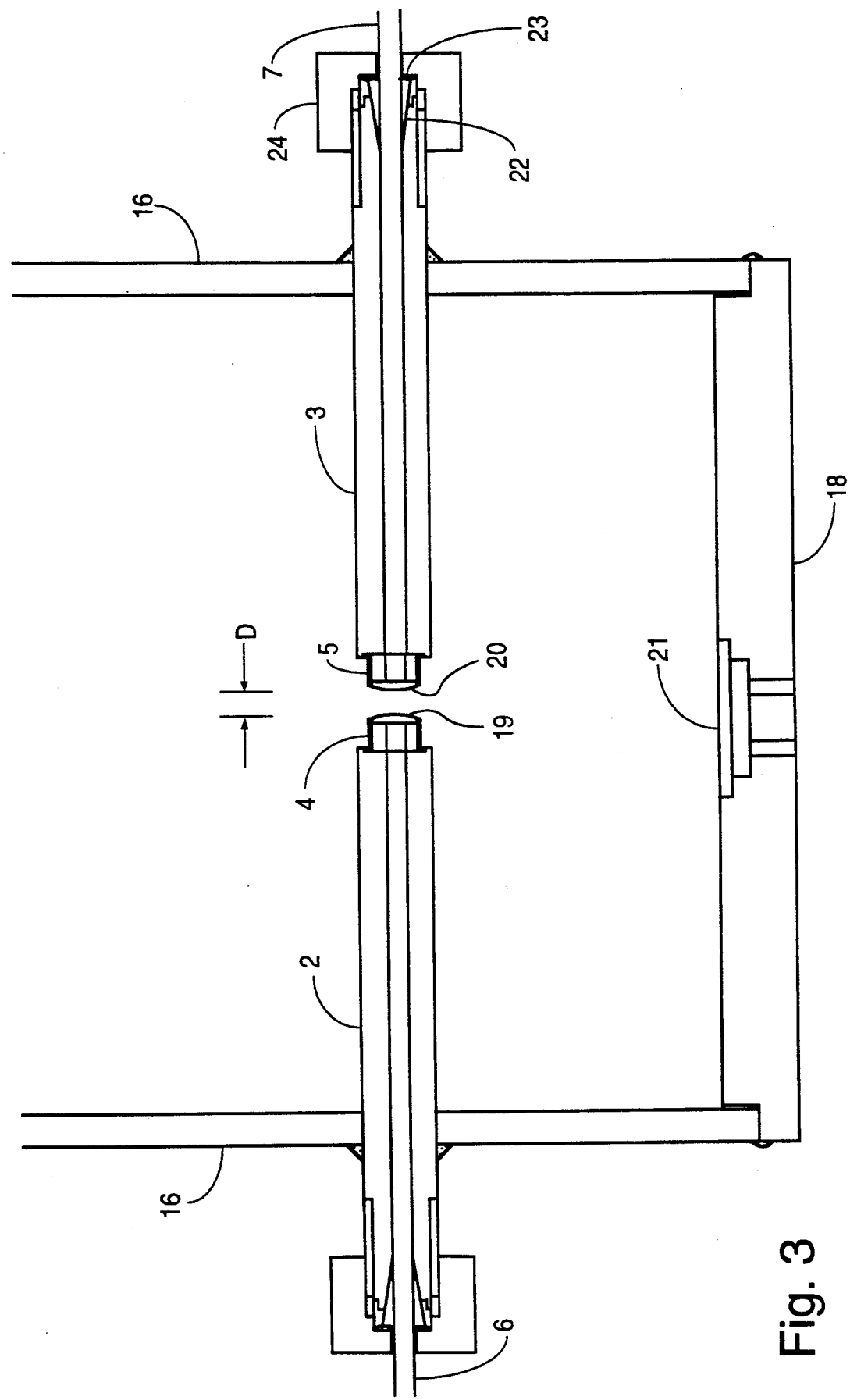
FIG. 3 is a cross-sectional view of the tubes and the end caps that extend into the container.

FIG. 3 shows the manner in which tubes 2 and 3 are welded to cylinder 16. Lens cap 4, holding a lens 19, is welded to an end of tube 2 to form a gas tight seal. Lens 19 is fused to lens cap 4 to form a gas tight optical window. Lens cap 5, holding a lens 20, is similarly welded to an end of tube 3. A filter 21 is attached to bottom 18 and a filter 29 is attached to top 17 to prevent resin 21 from entering tubes 10 and 11. The outside diameters of optical fibers 6 and 7 are slightly less than the inside diameters of tubes 2 and 3, respectively, so that the ends of optical fibers 6 and 7 are correctly aligned with lenses 19 and 20.

Figure 4:
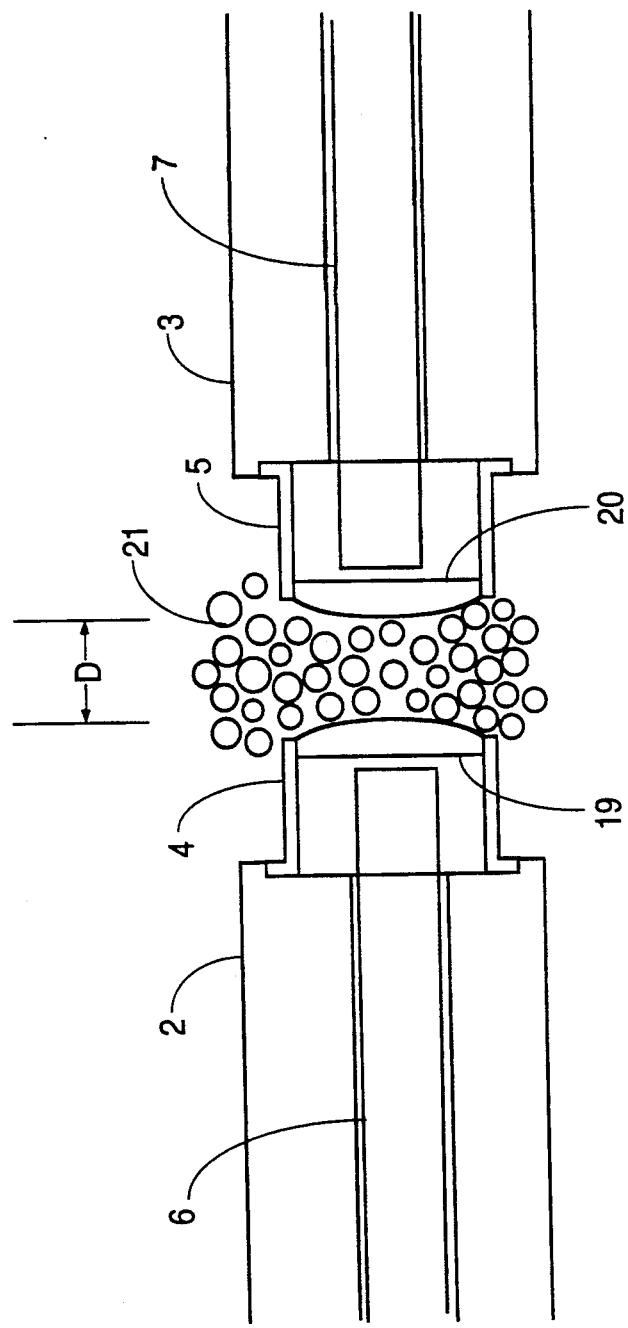
FIG. 4 is an enlarged cross-sectional view of the end caps, showing their relationship to typical resin particles in the container.
Figure 5:
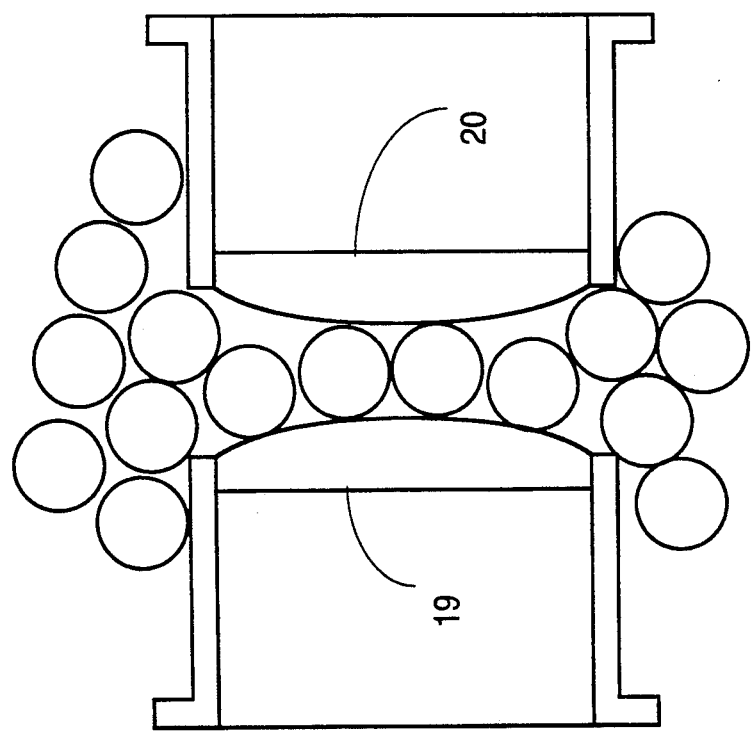
FIG. 5 illustrates an unacceptable spacing of the lenses in relation to the resin particle size.

FIG. 4 illustrates the positioning of lenses 19 and 20 and the particles of resin 21 between the two lenses. The spacing between lens 19 and lens 20 is dependent on the typical resin particle size and the ratio between the amount of light transmitted by resin 21 when it is in its chemically active and depleted states, respectively. It has been found that the optimal distance between lens 19 and lens 20 for the resin supplied by Millipore Corporation is between 0.050 and 0.150 inches. The particle size of the Millipore resin is typically 0.010 to 0.030 inches in diameter. The spacing between 19 and 20 should not be less than twice the diameter of the resin particles. Otherwise, as illustrated in FIG. 5, light may pass directly from lens 19 to lens 20 without intersecting the resin particles. In other words, when the spacing of the lenses is less than two particle diameters, an excessive amount of light is transmitted from lens 19 to lens 20 when the resin is in its opaque state. This makes it more difficult to discriminate between the opaque and translucent states of resin 21.

The maximum spacing D between lenses 19 and 20 is determined by the transparency of the resin in its depleted state as well as the intensity of the light source. In that state, the resin is translucent rather than totally transparent. Approximately 0.200 inches is the maximum distance that light can be transmitted through the Millipore resin in its translucent state.

Figure 6:
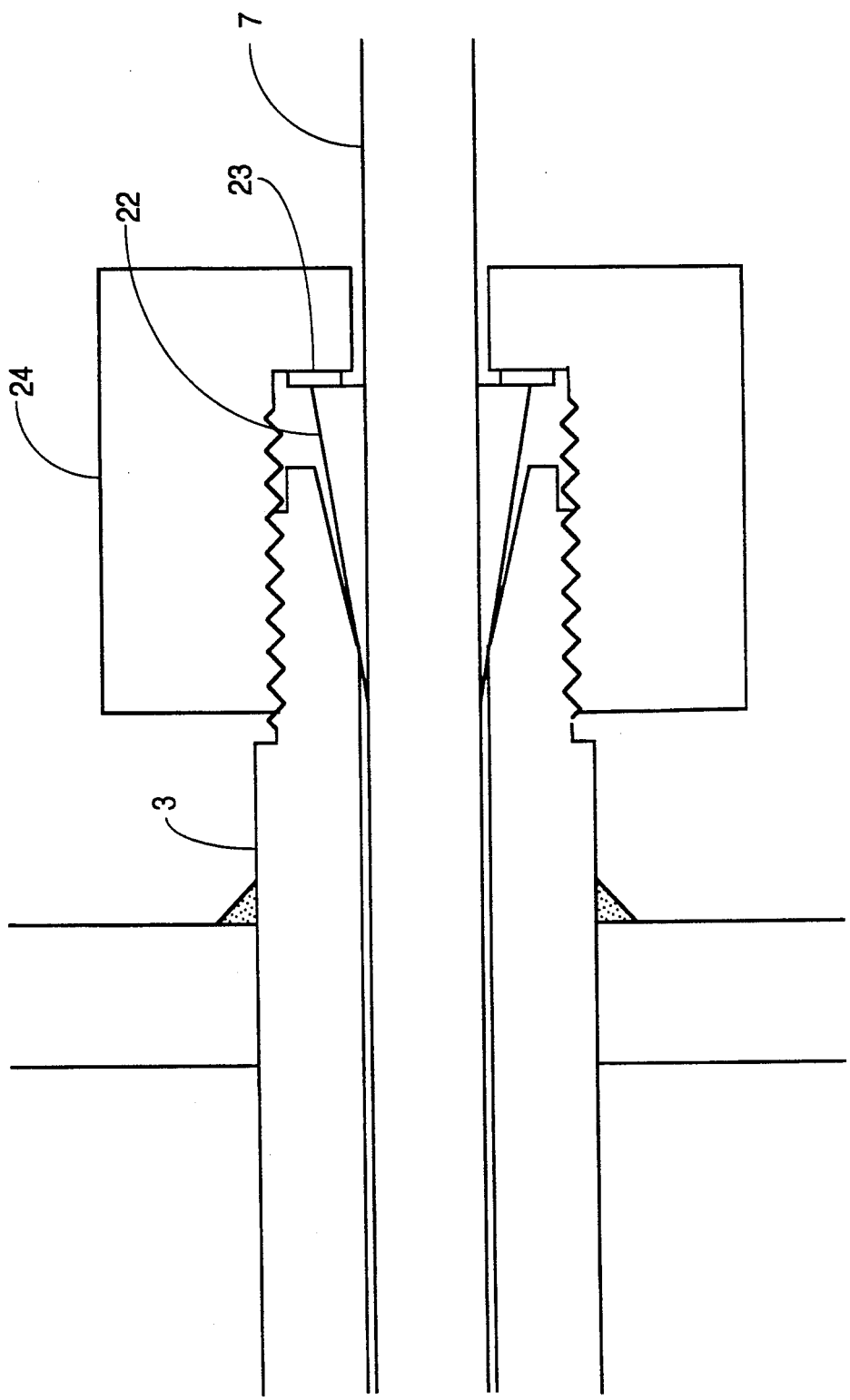
FIG. 6 illustrates a cross-sectional view of the secondary seal outside of the container.

FIG. 6 is a cross-sectional view of arrangement used to seal optical fiber 7 to tube 3 outside container 16. A gas tight seal is required at this location because many gases purified in container 1 are toxic or corrosive and must be prevented from escaping into the atmosphere should one of lenses 19 or 20 break. A gas tight seal is formed by crimping a ferrule 22 around optical fiber 7 by tightening a nut 24 onto a threaded end of tube 3. A washer 23 is used to minimize the rotation of ferrule 22 as nut 24 is tightened. The inside end of tube 3 is tapered slightly less (typically 2 degrees less) than the taper on ferrule 22 to ensure a proper crimp of ferrule 22 to optical fiber 7. A similar arrangement is used to form an outside seal between tube 2 and optical fiber 6.

Referring again to FIG. 1, the operation of the gas purifier with the optoelectronic detector can now be described Gas container 1 is assembled with the components shown in FIG. 2 and is leak-checked with helium to ensure that the assembly is gas tight. Container 1 is placed in a dry box (not shown) and is filled with resin 21 through tube 12 and then sealed by means of cap 26. Valves 29 and 30 are attached to tubes 31 and 32, and the valves are sealed off. The container is then shipped to the point of use where the unit is placed in a gas line. Optical fibers 6 and 7 are inserted into tubes 2 and 3 such that the ends of optical fibers 6 and 7 are touching or are in very close proximity to lenses 19 and 20. The assembly of ferrule 22, washer 23 and nut 24 is placed over a threaded end of tube 3 and a similar assembly is placed at the end of tube 2. Optical fibers 6 and 7 are then attached to light source and light receiver 9, respectively.

The gas line is then purged of impurities, typically by heating the gas line and subjecting it to a vacuum. When the gas line has been purged, valves 29 and 30 are opened and the unit is ready. When the resin becomes depleted between lenses 19 and 20, the amount of light received by light receiver 9 increases approximately ten-fold, at which time an alarm 25 is activated. Alarm 25 may provide an audible or visual signal. Advantageously tubes 2 and 3 are placed approximately one-fourth of the distance from the bottom of container 1 so that the alarm is sounded while approximately one-fourth of resin 21 is still active. This ensures continued gas purification until a replacement purification unit can be installed.

The foregoing embodiment is intended to be illustrative and not limiting. Many alternative embodiments will be apparent to those skilled in the art, all of which embodiments are included within the scope of this invention as defined in the following claims. For example, the principles of this invention are applicable to resins which are translucent when fresh and opaque when depleted, and to resins whose light transmissivity varies in any manner depending on whether they are fresh or depleted. Furthermore, the principles of this invention are applicable to any chemical reactant whose light transmissivity varies as the reactant goes from one state to another state.

I claim:

1. A device for detecting the chemical depletion of a solid chemical reactant capable of purifying gases, comprising:
   a container for holding said solid chemical reactant;
   an inlet tube and an outlet tube connected to said container, said inlet tube and said outlet tube and said container forming a flow channel for a gas to be passed through said solid chemical reactant;
   means for directing a beam of light through said solid chemical reactant;
   means for detecting the intensity of said beam of light after it passes through said solid chemical reactant, wherein the intensity of said beam of light provides an indication of the chemical depletion of said solid chemical reactant.

2. The device of claim 1 wherein said solid chemical reactant is a resin.

3. The device of claim 1 wherein said solid chemical reactant is opaque when it is unused and translucent when it is depleted.

4. The device of claim 1 wherein said solid chemical reactant is translucent when it is unused and opaque when it is depleted.

5. The device of claim 1 wherein the light transmissivity of said solid chemical reactant changes as said reactant moves from a first state to a second state.

6. A method of detecting the chemical depletion of a solid chemical reactant capable of purifying gases, comprising the steps of:
   directing a beam of light through said solid chemical reactant;
   measuring the intensity of said beam of light after it has passed through said solid chemical reactant, said intensity indicating the chemical depletion of said reactant.

7. The method of claim 6 wherein said solid chemical reactant is a resin.

8. The method of claim 6 wherein said solid chemical reactant is opaque when it is unused and translucent when it is depleted.

9. The method of claim 6 wherein said solid chemical is translucent when it is unused and opaque when it is depleted.

10. The method of claim 6 wherein the light transmissivity of said solid chemical reactant changes as said reactant moves from a first state to a second state.

* * * * *